United States Patent [19]

LeBoeuf et al.

[11] Patent Number: 5,523,290
[45] Date of Patent: Jun. 4, 1996

[54] ANTIPROLIFERATION FACTOR

[75] Inventors: Robert D. LeBoeuf, Birmingham; J. Edwin Blalock, Mountain Brook; Kenneth L. Bost, Birmingham, all of Ala.

[73] Assignee: University of Alabama at Birmingham Research Foundation, Birmingham, Ala.

[21] Appl. No.: 240,802

[22] Filed: May 10, 1994

Related U.S. Application Data

[63] Continuation of Ser. No. 805,101, Dec. 10, 1991, abandoned, which is a continuation of Ser. No. 308,160, Feb. 8, 1989, abandoned.

[51] Int. Cl.⁶ ............................ C07K 14/52; C07K 16/24; A61K 38/19
[52] U.S. Cl. ........................ 514/21; 530/350; 530/351; 530/387.1; 530/388.7; 530/388.73; 530/388.75; 530/388.8; 530/389.6; 530/389.7; 530/854; 530/395; 514/12; 424/85.1
[58] Field of Search ...................... 530/350, 351, 530/395, 387.1, 388.23, 388.7, 388.75, 388.8, 389.6, 389.7, 854; 424/85.1; 514/21, 12

[56] References Cited

U.S. PATENT DOCUMENTS 4,289,690  9/1981  Pestka et al. ............................ 530/351
5,187,077  2/1993  Gearing et al. ........................ 435/69.1

OTHER PUBLICATIONS

Hird et al. 1990. *Genes and Cancer*, (eds.) Carney et al., John Wiley and Sons, Ltd., N.Y., pp. 183–189.

*Primary Examiner*—Robert A. Wax
*Assistant Examiner*—Rebecca Prouty
*Attorney, Agent, or Firm*—Benjamin Aaron Adler

[57] ABSTRACT

Mammalian pituitary discovered anti-proliferation factor that inhibits in vitro cellular proliferation of lymphoid, neuroendocrine and neural cells but not of fibroblast or endothelial cells. The present invention is directed to this antiproliferation factor which has been named suppressin and is a protein of Mr 63,000, sensitive to reduction and has a pI of 8.1. Suppressin is provided as a cell free preparation or in homogeneous form. The invention provides methods to purify suppressin, antibodies against suppressin and their use recombinant DNA molecules encoding suppressin, and pharmaceutical compositions for inducing regression or inhibiting growth of tumor or cancel cells and autoimmune diseases.

18 Claims, 6 Drawing Sheets

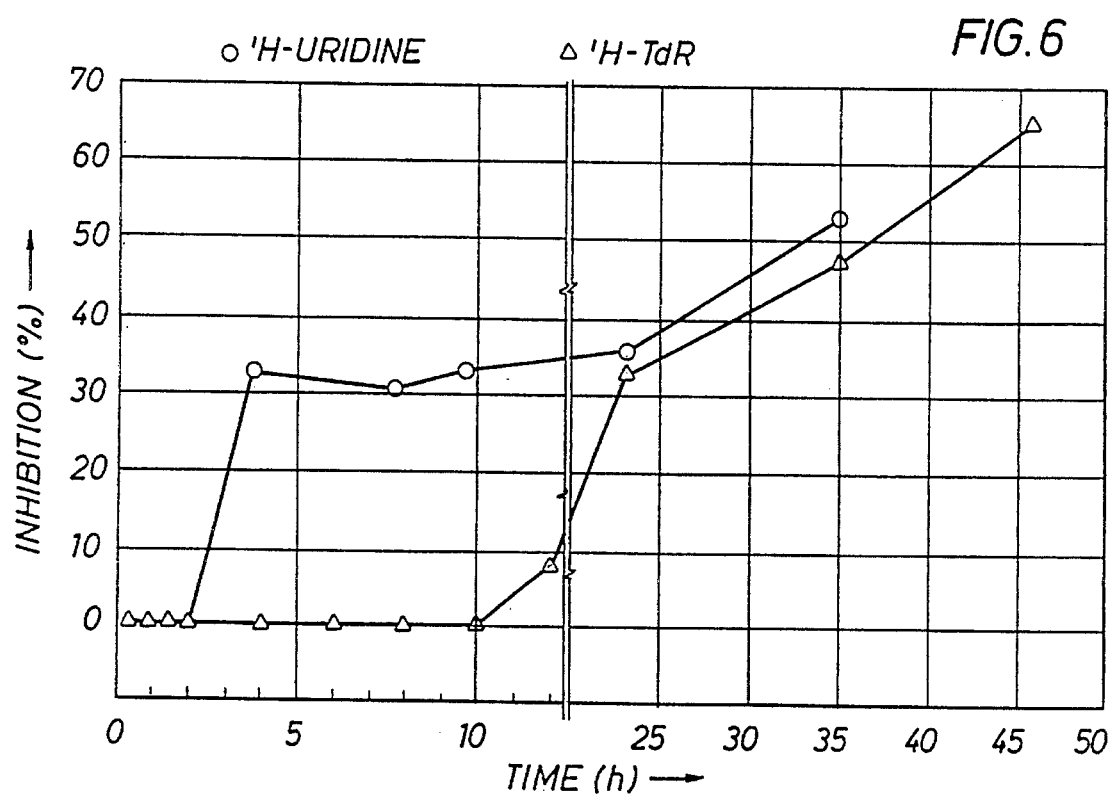

ANTIPROLIFERATION FACTOR

This is a continuation of application(s) Ser. No. 805,101 filed on Dec. 10, 1991 which is a Rule 60 Continuation of Ser. No. 308,160 filed on Feb. 8, 1989, both now abandoned.

FIELD OF THE INVENTION

The present invention is directed to mammalian suppressin, a newly discovered antiproliferation factor for normal and neoplastic cells of lymphoid, neuroendocrine and neural origin. Suppressin inhibits cell proliferation without being cytotoxic to the cell. Suppressin is provided as a cell-free preparation and in homogeneous form.

More particularly, suppressin is derived from pituitary extracts or cultured pituitary cells and comprises at least one subunit of an $M_r$ 63,000 protein having an intrachain disulfide and a pI of about 8.1.

BACKGROUND OF THE INVENTION

One of the hallmarks of homeostasis is the regulation of cell proliferation. Current regulatory models of cell proliferation include mechanisms for activation, modulation and inhibition of cell growth processes. The goal to understand the mechanisms for regulating cell proliferation lead to the discovery of an enormous number of stimulatory growth regulators, also known as growth factors. The search for inhibitory growth regulators has not been as extensive.

Novel regulatory molecules may participate in the bidirectional regulation between the neuroendocrine and immune systems. Hence, products from the pituitary gland may alter immune cell function(s) since experiments have shown that pituitary hormones affect lymphoid cell function [Johnson et al. (1982) Proc. Natl. Acad. Sci. U.S.A. 79: 4171–1414; Blalock et al. (1984) Biochem. Biophys. Res. Commun. 125: 30–34; and Lolait et al. (1984) J. Clin. Invest. 73: 277–280], and that lymphoid cells can synthesize and secrete pituitary hormones when stimulated by the appropriate hypothalamic releasing hormones [Smith et al. (1986) Nature (London) 322: 881–882].

Suppressin (SPN) is a novel regulatory molecule of neuroendocrine origin that inhibits cell proliferation. The size of SPN ($M_r$ 63,000) and its monomeric molecular structure are two characteristics relative to other endogenous inhibitors of cell proliferation, which indicate that it is novel. Transforming growth factor-beta (TGF-β) [Roberts et al. (1983) Biochemistry 22: 5692–5698; Roberts et al. (1985) Cancer Surveys 4: 683–705; and Massague (1984) J. Biol. Chem. 259: 9756–9761] and hepatic proliferation inhibitor (HPI) [McMahon, et al. (1982) Proc. Natl. Acad. Sci. U.S.A. 79, 456–460; Huggert, et al. (1987) J. Cell. Biochem. 35, 305–314; and McMahon (1984) J. Biol. Chem. 259, 1803–1806] are two endogenous inhibitors of cell proliferation for which the most information is available regarding their structure and biological activities. In contrast to SPN, both proteins are smaller than SPN (TGF-β, $M_r$ 25,000: HPI, $M_r$ ranging from 17–19,000 to 26,000) and they are secreted as homodimers. Additionally, SPN and HPI differ in their isoelectric point with SPN having a basic pI (8.1) and HPI with a pI of 4.65. SPN, TGF-β and HPI are similar in a general sense because they inhibit cell proliferation without showing cytotoxic effects. For example, TGF-β and HPI have been shown to inhibit epithelial cell proliferation in the presence of mitogens (Huggert et al.). Similarly, SPN inhibits splenocyte proliferation in the presence of mitogens. The specific differences in target tissues for the inhibitory activities of these three proteins suggests that they have distinct physiological functions. These three inhibitory molecules differ in the cell types affected as well as in their 50% inhibitory dose ($ID_{50}$). TGF-β has been shown to inhibit cells from several tissue types indicating that it is relatively nonselective [Roberts, et al. (19) Proc. Natl. Acad. Sci. U.S.A. 82: 119–123; and Tucker et al. (1984) Science 226: 705–707]. HPI and SPN are apparently more restricted in that they inhibit cells of hepatic origin (Huggett, et al. and Iype (1984) Mol. Cell. Biochem. 59: 57–80) or lymphoid origin, respectively. TGF-β, HPI and SPN inhibit cell proliferation at low molar concentrations. The $ID_{50}$ of SPN for splenocytes ($2.8\times10^{-9}$M) is higher than the $ID_{50}$ of TGF-β ($10.4\times10^{-12}$M) and HPI ($2.5\times10^{-12}$M) for rat liver epithelial cells (Huggett et al.) suggesting that they may be more potent inhibitors of cell proliferation than SPN. However, a wide variation has been observed in the response of cells to the same concentration of SPN indicating that response depends on the target cell. The structural and biological data obtained on SPN thus indicate that it is novel and different from TGF-β and HPI.

The significance of SPN is important since its biological activity is cytostatic and not cytotoxic. SPN may function as an endocrine, paracrine or autocrine modulator of cell proliferation. The production of neuroendocrine hormones that affect cells of the immune system suggests these hormones have a role as immunoregulatory molecules. If circulating neuroendocrine hormones, including SPN, directly affect immunocytes in vivo, then these hormones have paracrine or autocrine functions within the immune system. The de novo synthesis of SPN by $GH_3$ cells, its presence in normal tissues and the response of target cells (splenocytes) suggests endocrine regulation of the immune system.

Accordingly, SPN functions as an autocrine regulator of cell proliferation, especially since it has recently been detected in lymphocytes. The demonstration that primate kidney cells produce TGF-β [Tucker, et al. (1984) Proc. Natl. Acad. Sci. U.S.A. 81: 6757–6761], possesses receptors for TGF-β [Sporn, et al. (1985) Nature (London) 313: 745–747], and that their growth is inhibited by TGF-β (Tucker et al., 1984; Sporn et al., 1985) supports the general hypothesis that cell proliferation is controlled by autocrine regulation. Similar experiments with SPN and lymphocytes suggests that SPN is an autocrine regulator of lymphocyte proliferation, much in the same manner that TGF-β regulates kidney growth.

SUMMARY OF THE INVENTION

The present invention is directed to mammalian suppressin, a newly discovered antiproliferation factor for normal and neoplastic cells of lymphold, neuroendocrine and neural origin. Suppressin inhibits cell proliferation without being cytotoxic to the cell. Suppressin is provided as a cell-free preparation and in homogeneous form.

More particularly, suppressin is derived from pituitary extracts or cultured pituitary cells and comprises at least one subunit of an $M_r$ 63,000 protein having an intrachain disulfide and a pI of about 8.1.

Another aspect of this invention provides a process for the preparation of suppressin in various degrees of purity from bovine pituitary extracts. These preparations provide 35% ammonium sulfate-suppressin, DEAE-suppressin and homogeneous suppressin.

A further aspect of the present invention provides monoclonal and polyclonal antibodies to mammalian suppressin useful in purifying suppressin and detecting its presence in tissues or other preparations.

Yet another aspect of the present invention provides a process of purifying suppressin by affinity chromatography using anti-suppressin antibodies.

Still another aspect of this invention relates to an isolated or recombinant nucleic acid or cDNA encoding mammalian suppressin, and replicable expression vectors and transformants containing same.

A still further aspect of the present invention provides a pharmaceutical composition comprising an effective amount of mammalian suppressin, or an active derivative thereof, and a pharmaceutically acceptable carrier. These compositions are used in treating a variety of lymphoid and neuroendocrine diseases as well as inducing regression or inhibition of tumor or cancer growth.

BRIEF DESCRIPTION OF THE DRAWINGS

FIG. 6 shows an SDS-PAGE gel and autoradiograph illustrating that suppressin is constitutively produced by rat pituitary $GH_3$ cells.

DETAILED DESCRIPTION OF THE INVENTION

Figure 1:
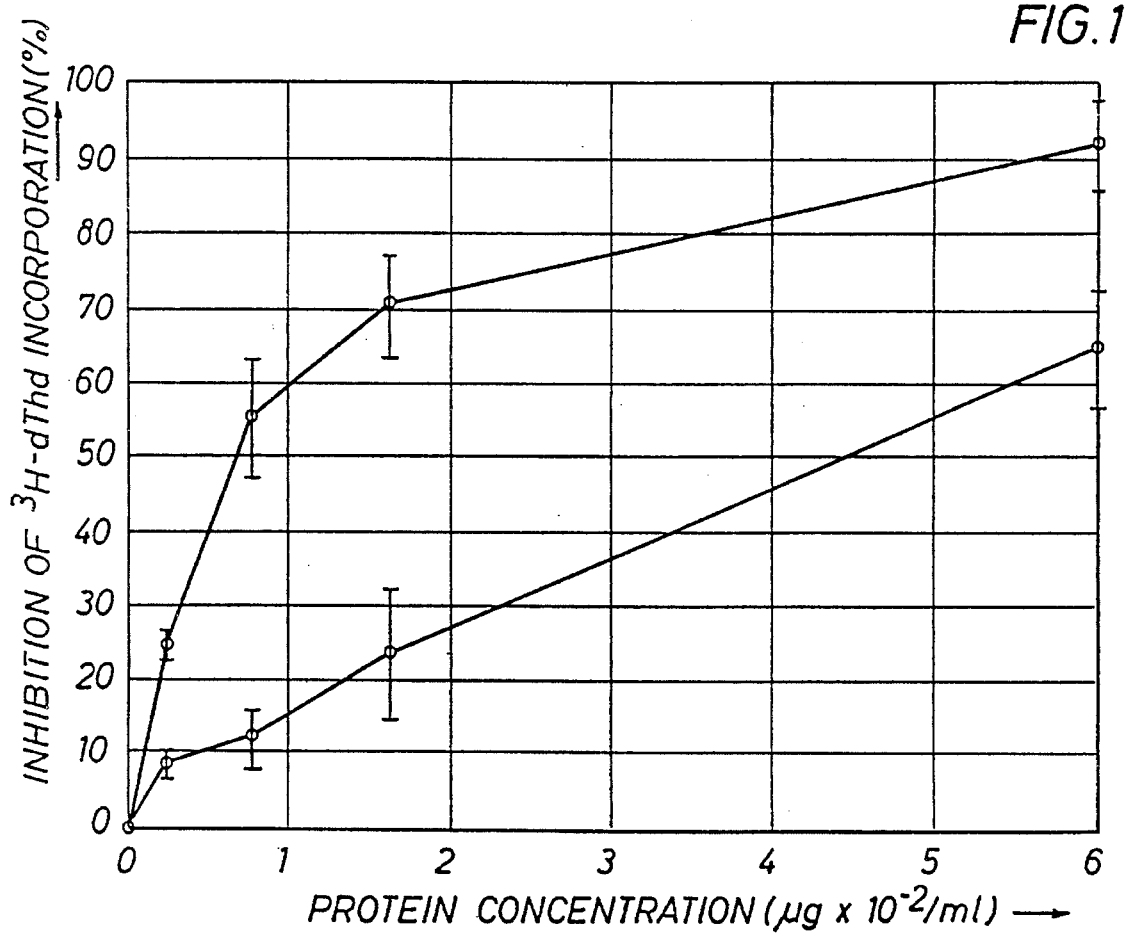
FIG. 1 is a graphical representation of the effects of a bovine pituitary extract (BPE) on Con A and LPS-stimulated splenocyte proliferation.

The present invention relates to a newly discovered tissue-specific antiproliferation factor. This factor is called suppressin (SPN). SPN is of mammalian origin and acts to inhibit cellular proliferation of normal and neoplastic lymphoid, neuroendocrine and neural cells without cytotoxic effects. In particular, SPN was identified as an active component in a bovine pituitary extract and found to inhibit proliferation of primary splenocytes, mitogen-stimulated splenocytes, primary B and T cells, IL-2 stimulated T-cells and various cultured cell lines in a tissue-specific manner. Cultured endothelial and fibroblast cell growth was unaffected by SPN. SPN is a protein having at least one subunit with an apparent molecular weight of 63,000 ($M_r$ 63,000), susceptability to reduction and an isoelectric point (pI) of about 8.1. These features distinguish SPN from pituitary-derived growth stimulatory or growth inhibitory factors. In accordance with the present invention and the methods contained herein, mammalian SPN is provided as a cell-free preparation or in homogenous form.

SPN activity is identified by testing primary splenocytes with a cell extract in a cell proliferation assay. A proliferation assay measures the amount of cell-associated $^3$H-thymidine during a growth period, and hence, is a measure of cellular DNA synthesis. Typically, cells are treated for a time period with the substance in question to permit expression of the desired characteristic or effect, and then pulsed with $^3$H-thymidine. Control cells are cultured in the same manner in the absence of the substance in question. The pulsed cells are harvested, and cell-associated radioactivity is determined. For growth inhibitory substances, including SPN, the percent inhibition is calculated from the difference in radioactivity taken up by the control and treated cells relative to the control cells. Bovine pituitary extract (BPE) or SPN inhibitory effects are assayed by exposing cells to these substances for about 36–72 h, preferably 40–50 h, before pulsing the cells for 12–18 h with $^3$H-thymidine. These cells are preferably primary splenocytes or mitogen-stimulated splenocytes.

Primary splenocytes, or spleen cells, and mitogen-stimulated splenocytes are sensitive to an SPN activity in a BPE and in lymphocytes. Primary splenocytes are tested for SPN response as described above. Inhibition of mitogen-stimulated proliferation is assayed by treating splenocytes concurrently with a mitogen and an SPN preparation or treating the cells with an SPN preparation at a specified time after addition of the mitogen. Splenocytes treated with Concanavalin A (Con A) pokeweed mitogen (PWM), phytohaemaglutinin (PHA) or bacterial lipopolysaccharide (LPS) are inhibited by SPN preparations.

The present invention provides SPN as a cell-free preparation or in homogeneous form. The cell-free preparations are obtained from mammalian pituitary tissue, preferably bovine pituitary tissue. An extract of these tissues is prepared by treating the pituitary tissue to lyse the cells by homogenization, sonication, or pressure which are techniques well known in the art. After lysis the extract is clarified, that is membranes and particulates are removed by centrifugation at g forces sufficient to pellet the membranes and particulates.

The cell-free preparations of SPN provided in accordance with the instant invention are 35% ammonium sulfate-SPN, DEAE-SPN and homogeneous SPN and are prepared by conventional purification means by following SPN activity in a cell proliferation assay.

The 35% ammonium sulfate-SPN is prepared from a bovine pituitary extract by sequential ammonium sulfate precipitation. A bovine pituitary extract is brought to 20% ammonium sulfate by adding a sufficient quantity of either solid ammonium sulfate or a saturated ammonium sulfate solution to achieve that concentration. After a precipitate forms, it is removed by centrifugation. The supernatent, containing the SPN activity, is brought to 35% ammonium sulfate and as before a precipitate forms. In this case the precipitate contains the SPN activity which is collected by centrifugation and resuspended in a suitable buffer. The resuspended precipitate is dialyzed until it is equilibrated in the buffer and the ammonium sulfate is removed. The resulting solution is called 35% ammonium sulfate-SPN and is active in inhibiting cell proliferation in accordance with the instant invention.

DEAE-SPN is prepared by subjecting 35% ammonium sulfate-SPN, that is the redissolved and dialyzed precipitate, to ion exchange column chromatagraphy. The effluent of the column is monitored for protein content by UV absorbance at 280 nm and the protein peaks pooled and tested in a splenocyte proliferation assay. The pooled, active fractions comprise DEAE-SPN.

In particular, ion exchange column chromatography is performed by loading the 35% ammonium sulfate-SPN onto an anion exchange chromatography column, preferably DEAE-53 (Whatman), which has been equilibrated in a suitable buffer of low ionic strength. A suitable buffer is 50 mM NaCl in, 10 mM Tris HCL, pH 8.0, but other buffers may be chosen and are readily selected by one of ordinary skill in the art. After the column is loaded it is extensively washed with the same buffer to remove non-binding components. This washing is followed by a stepwise change to 100 mM NaCl in 10 mM Tris, pH 8.0 before the bound material is eluted by a linear salt gradient of 0.1–1M NaCl in 10 mM Tris, pH 8.0. DEAE-SPN elutes between 150–200 mM NaCl under these conditions. When another buffer is used, or other commercially available anion exchange resins, the DEAE-SPN activity is monitored by the cell proliferation assay, thereby readily determining its elution point.

Homogeneous SPN is prepared from DEAE-SPN by preparative, native polyacrylamide gel electrophoresis (PAGE). DEAE-SPN is electrophoresed on a native PAGE gel, preferably a 10% gel with a 12 cm resolving zone. The gel is cut into strips and the proteins are electroeluted therefrom. The recovered proteins are tested in a proliferation assay, and the SPN activity is found in the strip from the 6–7 cm gel zone. There are two proteins in the 6–7 cm zone, and they have $M_r$ 63,000 and 15,000 as determined on a 12% native PAGE gel. These two proteins are electroeluted from the 12% native gel and tested for growth inhibitory effects. The $M_r$ 63,000 protein inhibited splenocyte proliferation whereas the $M_r$ 15,000 protein did not. The $M_r$ 63,000 protein is homogeneous SPN. One skilled in the art can readily determine other PAGE gel conditions to effect the necessary separations by adjusting the percentage acrylamide and the length of the resolving gel, and thereby may eliminate the need for a second round of electrophoresis and protein electroelution.

The amino acid composition of homogeneous SPN derived from a bovine pituitary extract is determined by standard methods (acid hydrolysis and quantitative analysis of the amino acids) with the following results:

| Amino Acid | Mole Percent |
| --- | --- |
| Ala | 7.5 |
| Arg | 4.9 |
| Asp or Asn | 9.7 |
| Cys | ND |
| Glu or Gln | 12.3 |
| Gly | 8.3 |
| His | 2.4 |
| Ile | 3.8 |
| Leu | 9.5 |
| Lys | 6.9 |
| Met | 0.3 |
| Phe | 3.9 |
| Pro | 6.2 |
| Ser | 7.3 |
| Thr | 7.0 |
| Trp | ND |
| Tyr | 3.3 |
| Val | 6.5 |

SPN purification can be scaled up to obtain large quantities of homogeneous SPN. Homogeneous SPN is useful as an immunogen to raise anti-SPN antibodies, to obtain its amino acid sequence which in turn provides a tool for cloning of its gene and as a therapeutic agent to inhibit proliferation cells.

The present invention provides monoclonal and polyclonal antibodies to mammalian SPN, especially bovine pituitary-derived SPN. Polyclonal and monoclonal antibodies are prepared by methods well known in the art. Extensive protocols for preparing, purifying, identifying, and use of monoclonal and polyclonal antibodies are found in Harlowe et al. (1988) *Antibodies: A Laboratory Manual*, Cold Spring Harbor Laboratory, Cold Spring Harbor, N.Y., 726p., which is incorporated herein by reference.

Polyclonal antibodies are conveniently prepared by immunizing rabbits with homogeneous SPN while monoclonal antibodies are conveniently prepared by immunizing mice with 35% ammonium sulfate sulfate-SPN, DEAE-SPN or homogeneous SPN. Alternatively, fragments or active derivatives of SPN may be used for immunization. These SPN fragments may be made by proteolytic digestion and purified by conventional means. SPN derivatives may be made by chemical modification of SPN or site-directed mutagenesis of the cloned SPN gene. Methods of identifying the desired antibody include ELISA assay using DEAE-SPN as the test material, Western or immunoblotting against DEAE-SPN or homogenous SPN, and other methods described in Harlowe et al. The antibodies are useful to affinity purify large quantities of SPN, rapidly assay cells for the production of SPN, determine the subunit structure of an SPN receptor, screen a cDNA library for SPN clones and to detect SPN in culture, tissues, tissue extracts and sera.

Accordingly another embodiment of the present invention provides a method of detecting mammalian SPN in a sample, especially cell cultures, tissues, tissue extracts or sera by contacting said sample with anti-SPN antibodies for a time sufficient and under conditions to form an antigen-antibody complex (e.g., an SPN-antibody complex) and subjecting said complex to a detecting means. The time required for antigen-antibody complex formation ranges from about 10 min to about 24 hours, depending on the antibody, the sample, temperature, buffers, and the detecting means. Again, Harlow et al. provide detailed protocols for the time and conditions required to form an antigen-antibody complex and detection thereof.

The detecting means may be direct or indirect; use radiolabelled, enzymatic-labelled, fluorescent-labelled, or heavy metal-labelled (colloidal gold or iron) antibodies; or be any of the means used in the methods outlined in Chap. 9–12 and 14 in Harlowe et al. including cell staining, immunoprecipitation, immunoblotting, immunoassay and immunodiffusion.

Anti-SPN antibodies are used to affinity purify SPN from pituitary extracts, partially fractionated extracts, or from culture media of cell lines that constitutively produce SPN (such as rat pituitary tumor cell line GH3). An affinity resin is prepared by covalently coupling anti-SPN antibodies to a solid matrix like Sepharose, Protein A-Sepharose or any other commercially available resin capable of covalently coupling proteins. The SPN-containing antigen preparation is loaded onto the resin and SPN is specifically bound thereto, the resin washed extensively to remove contaminants and unbound components, and finally, pure SPN is eluted from the resin and concentrated or dialyzed as desired. This technique is also known as immunoaffinity purification and detailed protocols therefor are found in Chap. 13 of Harlowe et al.

Another aspect of this invention comtemplates an isolated nucleic acid molecule, herein defined as RNA or DNA, encoding the gene for mammalian SPN or a derivative thereof, preferably encoding bovine pituitary-derived SPN. Similarly, the present invention contemplates a recombinant nucleic acid molecule comprising a DNA or cDNA for encoding mammalian SPN, especially bovine pituitary-derived SPN.

Methods for obtaining recombinant SPN cDNA are contained in Maniatis et al., 1982, in *Molecular Cloning: A Laboratory Manual*, Cold Spring Harbor Laboratory, New York, pp. 1–545 or another standard laboratory manual on recombinant DNA techniques. Generally, polyadenylated mRNA is obtained from $GH_3$ pituitary cells or any other cells known to produce SPN and fractioned on agarose gels. Aliquots of mRNA are then injected into *Xenopus laevis* oocytes for translation and oocyte extracts or culture media are assayed for SPN activity using the methods which are contained herein. The so-identified enriched fractions of mRNA translating into SPN active molecules are then used as template for cDNA. Alternatively, all the mRNA can serve as a template for making cDNA. In either case, libraries of cDNA clones are constructed in the PstI site of the vector pBR322 (using homopolymer tailing) or in a variety of other vectors (e.g. the Okayama-Berg cDNA cloning vectors, Messing cDNA cloning vecotrs, λgt11, and the like). Specific cDNA molecules in the vector of said libray are then selected by using specific oligonucleotides designed to encode at least part of an SPN amino acid sequence, said oligonucleotide having a nucleotide sequence based on amino acid sequences contained within SPN. The amino acid sequence is determined by subjecting homogeneous SPN or proteolytic fragements thereof to routine Edman degradation. Alternatively, libraries with cDNA in a λgt11 or related vector can be screened for SPN expression using the anti-SPN antibodies provided by the present invention. Once identified, cDNA molecules encoding all or part of recombinant SPN are then ligated into replicable expression vectors. Additional genetic manipulation is routinely carried out to maximize expression of the cDNA in the particular host employed.

Accordingly, SPN is synthesized in vivo by inserting said cDNA sequence into a replicable expression vector, transforming the resulting recombinant molecule into a suitable host and then culturing or growing the transformed host under conditions requisite for the synthesis of the polypeptides. SPN synthesized in this manner is recombinant SPN. The recombinant molecule defined herein should comprise a nucleic acid sequence encoding a desired polypeptide inserted downstream of a promoter, a eukaryotic or prokaryotic replicon and a selectable marker such as resistance to an antibiotic. A promoter is a nucleic acid sequence that is operably linked to the DNA encoding the desired polypeptide and said sequence being capable of effecting expression of the desired polypeptide. The recombinant molecule may also require a signal sequence to facilitate transport of the synthesized polypeptide to the extracellular environment. Alternatively, the polypeptide may be retrieved by first lysing the host cell by a variety of techniques such as sonication, pressure, dissintegration or toluene treatment. Hosts contemplated in accordance with the present invention can be selected from the group comprising prokaryotes (e.g., *Escherichia coli*, Bacillus sp., Pseudomonas sp., Streptomyces sp.) and eukaryotes (e.g., mammalian cells, yeast and fungal cultures, insect cells and plant cultures). The artisan will also recognize that a given amino acid sequence can undergo deletions, substitutions and additions of nucleotides or triplet nucleotides (codons). Such variations are all considered within the scope of the present invention.

SPN and DEAE-SPN inhibit the growth of normal and neoplastic lymphoid, neuroendocrine and neural cells. Inhibition of cell growth means cessation of DNA replication and cell division having the net effect of stopping cell multiplication. Hence, there is no further increase in cell number. Cultured fibroblast and endothelial cells are unaffected by SPN. Specifically, SPN inhibits growth in vitro of cells of the following types: human T cell leukemia, human T cell lymphoma, murine B cell leukemia, murine adrenal tumor, murine neuroblastoma x glioma, rat pituitary tumor, murine T cell, lymphocytic leukemia, and murine lymphoma.

Another aspect of the present invention provides SPN as a valuable therapeutic agent for inducing regression or inhibition of tumor and cancer growth in a mammal by administering an effective amount of SPN or an active derivative or fragment thereof. Regression, like inhibition, of tumor and cancer growth involves no further increase in cell number. However, unlike inhibition, regression encompasses a decrease in the number of tumor or cancer cells present. The decrease in cell number can be a direct consequence of inhibiting cell growth and may not be directly mediated by the therapeutic agent in question. A therapeutically effective amount of SPN will be 2 to 4 times the 50% inhibitory dose of the target cell and may range from about 0.1 ug to 2000 ug per kg body weight per day.

Cancer cells are generally undergoing abnormal growth so either inhibiting the growth of or killing of these cells is desired. Since SPN effectively inhibits lymphoid, neuroendocrine and neural cells, it is useful to treat cancer arising in these tissues. SPN can also be used to treat autoimmune or other immune system diseases, especially those diseases where there is proliferation of undesirable immune cells, for example, B cells that produce autoantibodies, especially autoantibodies involved in arthritis. Inhibition of the appropriate immune cells also reduces or even prevents transplantation or graft rejection.

Accordingly, the subject invention contemplates a method for inducing regression or inhibition of growth of cancer or tumor cells in mammals by administering a pharmaceutical composition containing an pharmaceutically effective amount of SPN or an active fragment or derivative thereof. Additionally, a method for inducing regression or inhibition of growth of cancer or tumor cells in a mammal is contemplated in which a nucleic acid molecule encoding SPN contemplated herein is introduced into an affected (i.e., cancerous or transformed) cell in such a manner that said nucleic acid molecule is expressed intracellularly but extrachromosomally of said cell or following integration into the genome of said cell. In this case, the nucleic acid molecule is carried to said affected cell and transferred into said cell by a second nucleic acid molecule (e.g., various viruses). The first nucleic acid molecule is manipulated such that it contains the appropriate signals for expression. That is, in accordance with the present invention, a method of inducing regression or inhibition of growth of tumors and cancer in a mammal is contempated comprising administering a first nucleic acid molecule encoding SPN, said nucleic acid being contained in a pharmacologically acceptable second nucleic acid carrier molecule such that said first nucleic acid enters a target cell and is either maintained extrachromosomally or integrates into the genome of said target all in such a manner that said first nucleic acid is expressed so as to produce an effective amount of SPN.

The active ingredients of the pharmaceutical compositions comprising SPN, are contemplated to exhibit excellent and effective therapeutic activity, for example, in the treatment of some cancers and tumors or immune system diseases. Thus, the active ingredients of the therapeutic compositions including SPN exhibit antitumor activity when administered in therapeutic amounts from about 0.1 ug to about 2000 ug per kg of body weight per day. The dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in a convenient manner such as by the oral, intraveneous (where water soluble), intramuscular, intravenous, intranasal, intradermal, subcutaneous, or suppository routes. Depending on the route of administration, the active ingredients of an SPN-containing pharmaceutical composition may be required to be coated in a material to protect said ingredients from the action of enzymes, acids or other natural conditions.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When SPN is suitably protected as described above, the active compound may be orally administered, for example, with an inert diluent or with an assimilable edible carrier, or it may be enclosed in hard or soft sheel gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparation should contain at least 1% of active compound. The percentage of the compositions and preparations may, of course, be varied and may conveniently be between about 5 to about 80% of the weight of the unit. The amount of active compound in such therapeutically useful compositions is such that a suitable dosage is obtained. Preferred compositions or preparations according to the present invention are prepared so that an oral unit dosage form contains between about 10 ug and 1000 ug of active compound.

The tablets, troches, pills, capsules and the like may also contain the following: A binder such as gum agragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage form is a capsule, it may contain, in addition to materials of the above type, a liquid carrier. Various other materials may be present as coatings or to otherwise modify the physical form of the unit dosage. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Unit dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health impaired as herein disclosed in detail.

The principal active ingredient, especially, SPN, is compounded for convenient and effective administration in pharmaceutically effective amounts with a suitable pharmaceutically acceptable carrier in dosage unit form as hereinbefore disclosed. A unit dosage form can, for example, contain the principal active compound in amounts ranging from 10 ug to about 1000 ug. Expressed in proportions, the active compound is generally present in from about 10 ug to about 1000 ug/ml of carrier. In the case of compositions containing supplementary active ingredients, the dosages are determined by reference to the usual dose and manner of adminstration of the said ingredients.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The following examples further illustrate the invention.

EXAMPLE 1

General Methods

A. General

Protein determinations were preformed by the method of Bradford (1976) *Anal. Brochen.* 72 248–254, using BSA as a standard. $^{125}$I-radioactivity was measured on a TM Analytical gamma counter (Model 1190). $^{3}$H- and $^{35}$S-radioactivity were measured on a TM Analytical liquid scintillation counter (Model 6892). SPN was radioiodinated using Iodogen in the procedure of Fraker and Speck (1978) *Biochem. Biophys. Res. Commun* 80: 849–857 Protein concentrations were performed using Centricon 30 concentrators (Amicon) which were centrifuged at 4° C. on a DuPont RC5B refrigerated centrifuge. The following reagents were purchased from the indicated vendors: Trypsin-Sepharose, Freunds adjuvant, Con A, LPS, penicillin and streptomycin (Signa Chemical Co.); Nutridoma-SP (Boehringer-Mannheim); Protein-A Sepharose, Iodogen (Pierce Chemical Co.) and $^{3}$H-thymidine, $^{35}$S-methionine, $^{125}$Iodine and $^{125}$I-Con A (DuPont). GH$_3$ cells were obtained from the American Type Tissue Culture collection.

B. Denaturing Electrophoresis

SDS-polyacrylamide electrophoresis (SDS-PAGE) was performed using 7.5% and 10% gels according to the method of Laemmli (1970) *Nature* 227: 680–685. Reduction of disulfide bonds prior to electrophoresis was accomplished by heating samples at 100° C. for 5 minutes in the presence of 11 mM dithiothreitol, and free sulfhydryl groups alkylated with 55 mM iodoacetamide. Protein bands were visualized by staining with either Coomassie blue or with silver. Two-dimensional PAGE was performed according to the method of O'Farrell (1975) *J. Biol. Chem.* 250: 4007–4021. The pI of SPN was determined from its migration relative to known commercially obtained standards (BioRad) that had been analyzed by isoelectric focusing under identical conditions. Isoelectric focusing gels contained 4% polyacrylamide and 8M urea. The second dimension gel was a 10% polyacrylamide gel.

C. Animals

C57/B6 mice (20–25) were purchased from Jackson Laboratories, Bar Harbor, Me. New Zealand white rabbits were obtained from Myrtle's Rabbitry, Franklin, Tenn.

D. Mouse Spleen Cell Preparation

Mouse spleens were aseptically removed and placed in RPMI 1640 medium/5% FBS/penicillin (100 U/ml)/strephtomycin (100 ug/ml). Single cell suspensions were obtained by gently teasing isolated spleens with forceps, washing twice with medium, and resuspending 1–2×10 cells/mi. Cell viability was determined by trypan blue exclusion.

E. Splenocyte Basal and Mitogen-Induced Proliferation Assays

Splenocyte proliferation assays were performed in 96-well microtiter tissue culture plates (Falcon Plastics). Splenocytes (1–2×10 cells/well) in 100 ul of RPMI 1640 (Gibco)/5% FBS (Gibco)/Penicillin (100 U/ml)/Streptomycin (100 ug/ml) medium were placed in a microtiter well containing either 50 ul of sterile Buffer A or 50 ul of the extract of SPN preparation to be tested. Splenocytes were cultured in 5% CO$_2$ at 37° C. for 48. After 48 h, 500 nCi of $^{3}$H-dThd in culture media was added to each well and the cells cultured an additional 12 h. The cells were then harvested on glass fiber filters using a multiple cell harvester (Whitaker). Filters were air dried and the cell associated $^{3}$H-radioactivity from each microtiter well determined. Six replicates for each experimental treatment and dilution were performed. The mean ±SEM for each treatment was determined and the reduction in proliferation expressed as a percentage of the mean control cell $^{3}$H-dThd incorporation.

F. Suppressin Preparation and Purification

1. Pituitary Tissue Preparation and Extraction

Frozen whole bovine pituitaries (Pell Freeze) were thawed in Buffer A (150 mM NaCl/10 mM HEPES/pH 7.4) on ice and then rinsed twice with Buffer A. Connective tissues were dissected away, whole pituitaries were minced into approximately 0.5 cm pieces in 5 ml of Buffer A/g weight. tissue and homogenized (Tekmar Corp.). All of the procedures above were performed on ice. The homogenate was filtered through glass wool and the filtrate centrifuged at 7,100×g for 10 minutes at 4° C. The resulting supernate was clarified by centrifugation at 40,500×g for 1 h at 4° C. followed by filtering through a 0.45 um membrane (Millipore).

2. Ammonium Sulfate Precipitation of Pituitary Extracts

The filtered pituitary extract was brought to 20% saturation with $(NH_4)_2SO_4$ placed on ice with stirring for 1 hour and then centrifuged at 32,000×g at 4° C. for 15 minutes. The supernate was decanted, the pellet discarded and the supernate brought to 35% $(NH_4)_2SO_4$ stauration. After centrifugation at 32,000×g for 15 minutes at 4° C., the supernate was discarded and the precipitate was redissolved in 50 mM NaCl/10 mM Tris/pH 8.0 (Buffer B) and dialyzed against Buffer B until the pH and conductivity of the extract was the same as Buffer B. The extract was used at this point for ion-exchange chromatography. This preparation is called 35%-ammonium sulfate-suppressin.

3. Ion-Exchange Chromatography

A DEAE-53 (Whatman) ion exchange column (3×30cm) was equilibrated in Buffer B until the column effluent was the same pH and conductivity as Buffer B. The sample was loaded on the column (1 ml/min.), the column washed with 100 ml of Buffer B, 100 ml of 100 mM NaCl/10 mM Tris/pH 8.0 and then a linear gradient from 100 mM NaCl to 1M NaCL in Buffer B was used to fractionate the extract. Fractions (6 ml) were collected, all peaks were pooled and dialyzed against Buffer A. Each pool was tested in a splenocyte proliferation assay to determine which pool contained inhibitory activity. Suppressin at this stage of purification is called DEAE-SPN.

4. Preparative Native PAGE

Discontinuous preparative native or non-denaturing PAGE was performed on DEAE-SPN using Laemmli's published acrylamide and buffer concentrations except SDS was omitted from all buffers. Briefly, DEAE-SPN (100–500 1ug) was dialyzed against 10 mM Tris/100 mM glycine/pH 7.0 and then diluted with an equal volume of 2× PAGE sample buffer and electrophoresed through either a 10% or 12% cm resolving polyacrylamide gel at constant current (20 mA/gel) until the tracking dye was 1 cm from the bottom of the gel. A vertical gel strip was removed and stained with silver. The remainder of the gel was sliced into horizontal 1.5 cm zones, diced into approximately 2 mm squares and electroeluted (Isco) at 1 Watt for 12 at 4° C. in 1 mM Tris, 10M glycine pH 8.0. The eluted proteins were recovered and dialyzed against Buffer A before use in splenocyte proliferation assays and SDS-PAGE analysis. At this point, suppressin was apparently purified to homogeneity, and it is refered to as SPN.

5. Amino Acid Analysis

A lyophilized sample (10 ug) of SPN was dissolved in 10 ul of 0.2N HCl, 200 mM lithium citrate pH 2.2 and then hydrolyzed in 100 ul of 6N HCl/1% phenol for 24 hours at 100° C. The sample was then analyzed on a Beckman 6300 amino acid analyzer and data processed using PE/Nelson 2600 chromatography computer software.

G. Polyclonal Anti-Suppressin Antibodies

Pure SPN (10 ug) was subjected to SDS-PAGE on 12% gels, the band excised from the gel, emulsified in 4 ml of PBS with complete Freund's adjuvant (50:50 v/v) and injected subcutaneously into two white female New Zealand rabbits (2 ml/animal). Pre-immune sera was obtained from each animal, and they were re-immunized and bled every 10 days for 30 days. Immunoglobulins were purified from rabbit serum by chromatography on Protein-A Sepharose followed by chromatography over an affinity column containing DEAE-SPN (100 ug/ml resin) and the presence of anti-SPN antibodies determined by an ELISA.

H. ELISA Assays

Microtiter wells were coated with DEAE-SPN (10 ug/ml) in 0.1M sodium carbonate pH 9.0 at 4° C. for 12 h. The plate was washed with PBS and then with 0.5% ovalbumin/0.1% Tween-20 in PBS. Protein A purified Ig from anti-SPN serum at various dilutions was added to each well, the plate incubated for 2 h at 22° C. and then the plate was washed 3 times with 0.1% ovalbumin-PBS (w/v). A secondary antibody, anti-rabbit Ig conjugated to alkaline phosphatase (Boehringer-Mannheim), was added to each well, the plate incubated at 22° C. for 1 h and then washed 3 times with PBS-Tween. 200 ul of p-nitrophenol phosphate (1 mg/ml) was added to each well and the reaction allowed to proceed at room temperature for 15 min. The reaction was stopped by adding 50 ul of 3M NaOH to each well and the $A_{405}$ of each well was determined. As a control for nonspecific Ig binding to wells, Protein A purified pre-immune rabbit Ig at the appropriate concentrations was used as the primary antibody.

I. Western Blotting

Samples were subjected to SDS-PAGE on 10% gels and then transferred to nitrocellulose using standard methods Burnette (1981) *Anal. Biochem.* 112 195–203. After transfer, the gel was stained with coomassie blue to determine efficiency of transfer. Nitrocellulose filters were processed for immunostaining by treatment with 3% normal goat serum in PBS for 30 min. at room temperature and then with affinity purified anti-SPN antibodies, diluted 1:500 with PBS containing 1% normal goat serum (Vega Laboratories). After washing the presence of antibody was detected using a biotinylated goat anti-rabbit Ig according to the manufacturer's protocol (Vega Laboratories).

J. Metabolic Radiolabelling of SPN

Rat pituitary cells ($GH_3$) were cultured for 48 hours in RPMI 1640 medium/5% FBS/Penicillin (100 U/ml)/Streptomycin (100 ug/ml) containing 0.1 mM L-methionine and 40 uCi/ml of $^{35}$S-methionine. The conditioned media from these cells was chromatographed over an anti-SPN antibody affinity column. The column was washed until the $A_{280}$ returned to baseline. The bound proteins were eluted with 100 mM of NaCl/100 mM glycine/pH 3.2, analyzed by SDS-PAGE and for SPN bioactivity. Samples analyzed by SDS-PAGE were stained with Coomassie blue and treated with EN³HANCE (DuPont). The gel was dried on filter paper then exposed to X-OMAT AR film (Eastman Kodak). Autofluorographic exposures were done for 1–2 at −70° C. using Cronex Lightning plus intensifying screens (DuPont).

EXAMPLE 2

Cellular Response to Suppressin in a Bovine Pituitary Extract

A clarified bovine pituitary extract (BPE) inhibited 3H-thymidine ($^3$H-dThd) uptake in unstimulated primary splenocytes. The amount of cell-associated $^3$H-radioactivity in BPE-treated splenocytes from five separate experiments was an average of 93%±1.3% less than that of control cells. BPE was not cytotoxic since the cell viability, as determined by trypan blue dye exclusion, of BPE-treated splenocytes and control cultures was essentially identical after 60 h in culture (control=80% viable, BPE-treated=81% viable). Decreases in $^3$H-dThd incorporation was representative of a reduction in the proliferation of BPE treated cells since these reductions in $^3$H-thymidine incorporation were directly correlated with the number of cells in treated cultures at the end of an experiment Studies on the biochemical nature of the proliferation inhibitor in BPE indicated that it was a protein, since the inhibitory activity was trypsin-sensitive and heat labile. For these assays, shown in Table 1, samples of BPE (500 ug) were incubated with the indicated enzyme covalently linked to Sepharose 4B (Pharmacia) for 3 h at 37° C. The insoluble protease was removed by centrifugation and the treated samples tested in the splenocyte proliferation assay. For heat denaturation experiments, samples were treated at the indicated temperature for 3 min and then tested in the splenocyte proliferation assay.

Additional experiments showed BPE would also inhibit the proliferation of splenocytes stimulated with the T-lymphocyte mitogen, Con A, and the B-lymphocyte mitogen, LPS. Murine splenocytes ($2 \times 10^6$/ml) were cultured for 48 h in the presence of varying concentrations of BPE with either Con A (2 ug/ml) or LPS (50 ug/ml). Cells were then cultured an additional 12 h with $^3$H-dThd, the inhibition of proliferation was determined from the difference between treated and control cell associated $^3$H-radioactivity.

As illustrated in FIG. 1, BPE did in fact significantly suppress cell proliferation as reflected in the incorporation of $^3$H-dThd in a dose-dependent manner in both Con A and LPS-stimulated splenocyte cultures. The inhibitory effects of BPE was titrated and the use of selective mitogen suggested that T-lymphocyte proliferation was reduced to a greater extent than was B-lymphocyte proliferation.

EXAMPLE 3

Purification and Biochemical Characterization of Suppressin

Bovine pituitaries were extracted into buffer and clarified as described in the Methods section. Sequential $(NH_4)_2SO_4$ precipitation of aqueous pituitary extracts showed that the antiproliferative component was recovered in the 25–30% precipitates (Table 8) and quantitatively recovered by sequentially precipitating with first 20% $(NH_4)_2SO_4$, and then 35% $(NH_4)_2SO_4$. This recovery is accomplished by first bringing the extract to 20% saturation, then centrifugating the extract and discarding the pellet. The supernatent contained all of the antiproliferative activity which was then precipitated by bringing the solution to 35% saturation. SDS-PAGE analysis showed that the 35% $(NH_4)_2SO_4$ precipitate contained 45–50 protein species, representing 8–10% of the protein present in the initial extract. This procedure was performed more than 50 times, and consistently produced the same pattern.

Figure 2:
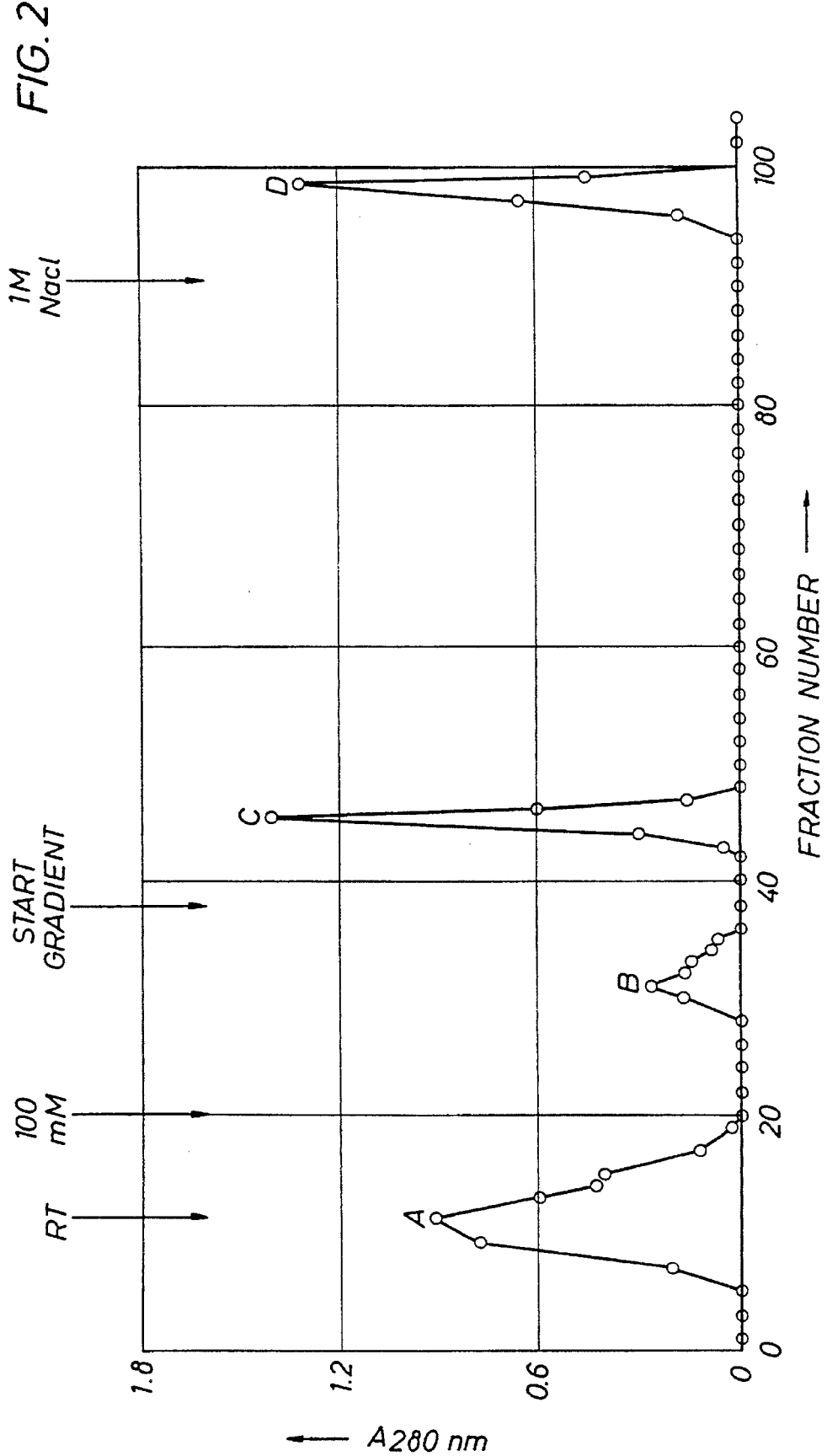
FIG. 2 shows the chromatographic elution profile of 35%-ammonium sulfate suppressin fractionated on a DEAE-53 ion exchange column.
Figure 3:
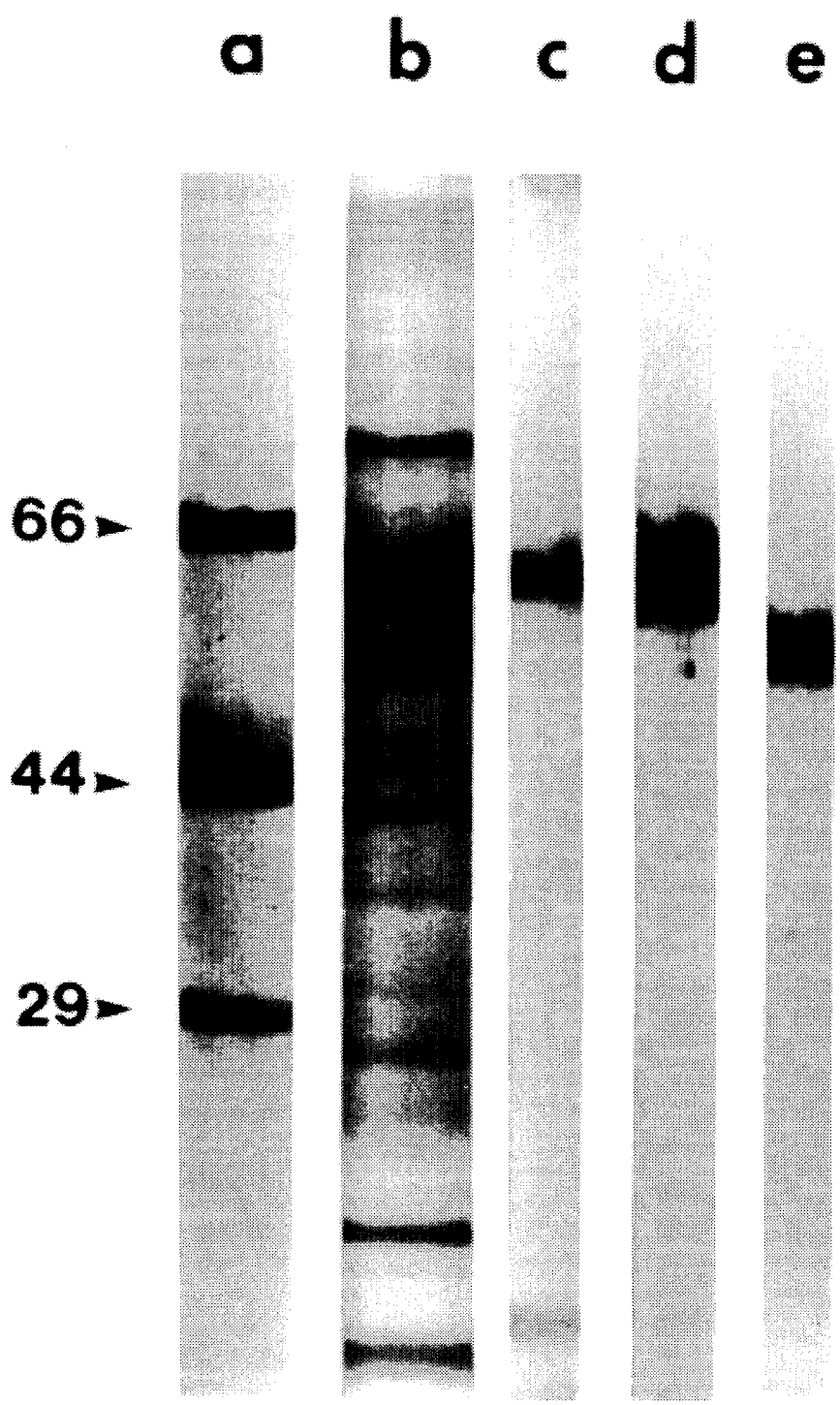
FIG. 3 shows an SDS-PAGE illustrating the purification of and the reduction of bovine pituitary-derived suppressin.

The 35% $(NH_4)_2SO_4$ precipitate from 50 g/wet wt of bovine pituitaries was redissolved in 50 mM NaCl/10 mM Tris/pH 8.0 (Buffer B) and loaded on a DEAE-53 anion exchange column. The NaCl concentration was increased stepwise to 100 mM and then the bound proteins were eluted with a linear 100 mM to 1M NaCl gradient (FIG. 2). The peak fractions were pooled, dialyzed, concentrated and tested for inhibitory activity. Peak C, which eluted between 150–200 mM NaCl, at 13.7 ug/ml was the only sample that inhibited $^3$H-dThd incorporation (67%) had approximately 9 major protein species ranging in Mr from 110,000 to 20,000 in DEAE Peak C (FIG. 3, Lane b). The Peak C preparation is called DEAE-SPN.

Suppressin was purified to apparent homogeneity by preparative native gel electrophoresis under nondenaturing conditions. DEAE-SPN (100–500 ug) was electrophoresed on a preparative 12 cm, 10% native polyacrylamide gel. After electrophoresis, the gel was cut in 1.5 cm strips and proteins in each gel strip were electroeluted. After electrophoresis, the gel was cut 1.5 cm in the gel inhibited splenocyte proliferation 62% while fractions electroeluted from all other strips of the gel showed no inhibitory activity in this assay. SDS-PAGE analysis showed that this region of the gel contained 2 proteins, one with an electrophoretic mobility corresponding to 63 kD and one to 15 kD (FIG. 3, Lane C). This two-protein fraction was electrophoresed again on a 12% native polyacrylamide gel which resolved the 63 kD and –15 kD bands. Each polypeptide zone was cut from the gel, electroeluted, and tested in a splenocyte proliferation assay (100 ng/ml). Splenoctye proliferation was inhibited 55% by the 63 kD moiety showed a single protein band at 63 kD under reducing conditions and one band which migrated at 58 kD under nonreducing conditions (FIG. 3, Lanes D and E). These analyses showed that SPN is a monomeric protein and suggests that it has intrachain disulfide bonds.

Homogeneity of SPN was assessed by SDS-PAGE analysis, 2-D PAGE, and HPLC. SDS-PAGE analysis of SPN showed a single protein band, however, the band was broad which could be due to the presence of contaminating proteins with an $M_4$ similar to SPN. Therefore, the purity of SPN was analyzed by isoelectric focusing on two-dimensional PAGE. These results showed that SPN had in fact been purified to homogeneity since only one spot was present on the silver strained gel. Finally, the purified SPN showed only one peak when chromatographed on reverse-phase HPLC. The amino acid composition of SPN is shown in Table 2.

The amount of SPN in pituitaries ranged from 8–63 ng/g wet wt of tissues. This estimate is based on the quantitation of the SPN concentration in an extract by silver strained SDS-PAGE analysis and then the intensity of the SPN band was compared to the intensity of known concentrations of protein standards. These estimates indicated that there was 2–15 ng of SPN/g wet wt of pituitary tissue and were in good agreement with the quantitation of SPN by amino acid composition analysis. Additionally, the efficiency of the extraction procedure was also determined. Affinity purified SPN (see example 8) was radioiodinated and $1.68 \times 10^6$ cpm of $^{125}$I-SPN was added to homogenized BPE from 10 g of pituitary tissues. The results of this experiment showed that the recovery of $^{125}$I-SPN from an extract after purification was 24%. Collectively, these results indicate that 8–63 ng of SPN are present in 1 g (wet wt) of pituitary tissues.

EXAMPLE 4

Production of Monospecific Polyclonal Anti-SPN Antibodies

Affinity-purified anti-SPN antibodies were prepared in New Zealand white rabbits that were immunized with affinity purified SPN. The presence of anti-SPN antibodies in the sera of immunized rabbits was determined by ELISA (Table 3) which showed that the affinity-purified Ig from serum taken 60 d post-immunization contained antibodies that cross-reacted with one of the components in DEAE-SPN, presumably SPN. The unbound or run-through Ig contained no antibodies that cross-reacted with components of DEAE-SPN. Western analysis with DEAE-SPN and immunoblotting showed that the affinity-purified SPN antibodies were monospecific since they only recognized SPN in the DEAE-SPN.

Figure 4:
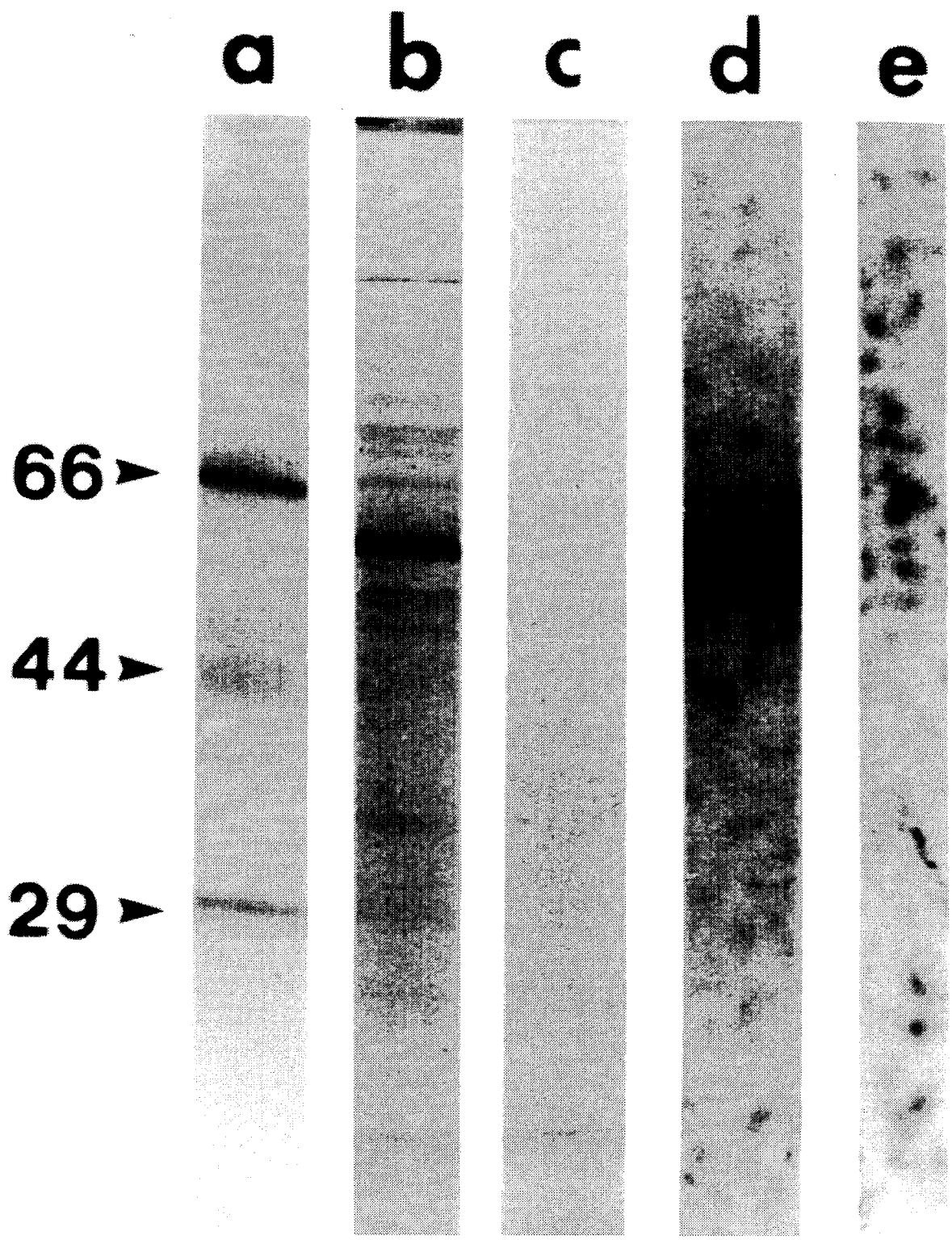
FIG. 4 shows a Western blot illustrating the specificity of polyclonal antibodies against suppressin.

The blot is shown in FIG. 4 and the lanes are A, Molecular weight standards; B, Coomassie blue stained gel strip-before transfer; C, Coomassie blue strained gel strip-after transfer; D, gel strip probed with anti-SPN antibody; E, gel strip probed with pre-immune sera.

EXAMPLE 5

Cellular Proliferation Response to Suppression

The effect of suppressin on mitogen-stimulated splenocytes was examined in a cell proliferation assay. Murine splenocytes ($3 \times 10^6$) were treated with DEAE-SPN (2.5 ug/ml) in the presence of Concanavalin A (Con A, 2 ug/ml), phytohaemaglutinin (PHA, 10 ug/ml), pokeweed mitogen (PWM, 10 ug/ml) or bacterial lipopolysaccharide (LPS, 50 ug/ml). Control cells were cultured with the appropriate mitogen in the absence of suppressin. Table 4 shows that Con A, PHA and PWM inhibited proliferation by greater than 90% whereas LPS only inhibited proliferation by about 65% suggesting that suppressin may differentially inhibit B and T cell populations.

The kinetics of inhibition of Con A-activated splenocyte proliferation was examined by adding SPN at various times after Con A and determining the incorporation of $^3$H-thymidine. Murine splenocytes ($2 \times 10^6$) were cultured with 2 ug/ml Con A and 25 ul of DEAE-SPN (3 ug/ml) was added at various times. After 48 h in culture, the cells were cultured with $^3$H-thymidine for 18 h and percent inhibition was calculated. The results (Table 5) indicate that concomitant or later addition of SPN significantly decreases the incorporation of $^3$H-thymidine.

The dose response of Con A-stimulated splenocytes to homogeneous SPN was determined. Murine splenocytes ($2 \times 10^6$ cells/ml) were cultured with 2 ug/ml Con A and the indicated concentrations of homogeneous SPN for 36 h, $^3$H-dThd was added and the cells cultured for an additional 18 h. The results in Table 6 indicate that 50% inhibition ($ID_{50}$) of $^3$H-thymidine incorporation occurs at $2.8 \times 10^{-9}$M SPN.

Inhibition of cellular proliferation by SPN was reversible. Cells treated with DEAE-SPN for 24 h incorporated $^3$H-thymidine at a level near control cells upon removal of SPN. Control cultures incorporated 42,972±1,842 cpm; cultures treated with SPN and then removed, incorporated 36,252±2,876 cpm; and SPN-treated for the duration of the experiment incorporated 19,865±1592 cpm.

The reduction in the amount of cell associated $^3$H-thymidine in SPN treated cells was not due to either the binding of thymidine by SPN or the degradation of thymidine by SPN or other extract-associated enzymes such as thymidine phosphorylase. Control studies indicated that cell associated $^3$H-thymidine was essentially the same for cells that received $^3$H-thymidine or $^3$H-thymidine that had been incubated with BPE for 5 h at 37° C. prior to the addition to cultures.

Finally, it is unlikely that SPN is either modifying components in the culture medium or vice versa and that it is this modified molecule that is responsible for the observed biological activity. Cell proliferation in Con A-stimulated splenocyte cultures treated with SPN in media with either 5% FBS or in serum-free medium supplemented with 2% Nutridoma SP were inhibited similarly at 60% and 76%, respectively. These results suggested that SPN was acting directly and did not require activation or association with serum components.

EXAMPLE 6

Other Cellular Responses to Suppressin

The effects of SPN on protein synthesis were examined by the ability of splenocytes to incorporate $^{35}$S-methionine. Murine splenocytes (5×10$^6$ cells/ml) were cultured in RPMI 1640 medium containing 302 uCi/ml $^{35}$S-methionine for 24 h in the presence of 1.3 nM SPN or in its absence. The cells were harvested and the cell associated radioactivity was determined. SPN-treated cells incorporated 51% less $^{35}$S-methionine than did control cells, 45,860±8,535 versus 93,330±9,825 cpm, respectively.

Figure 5:
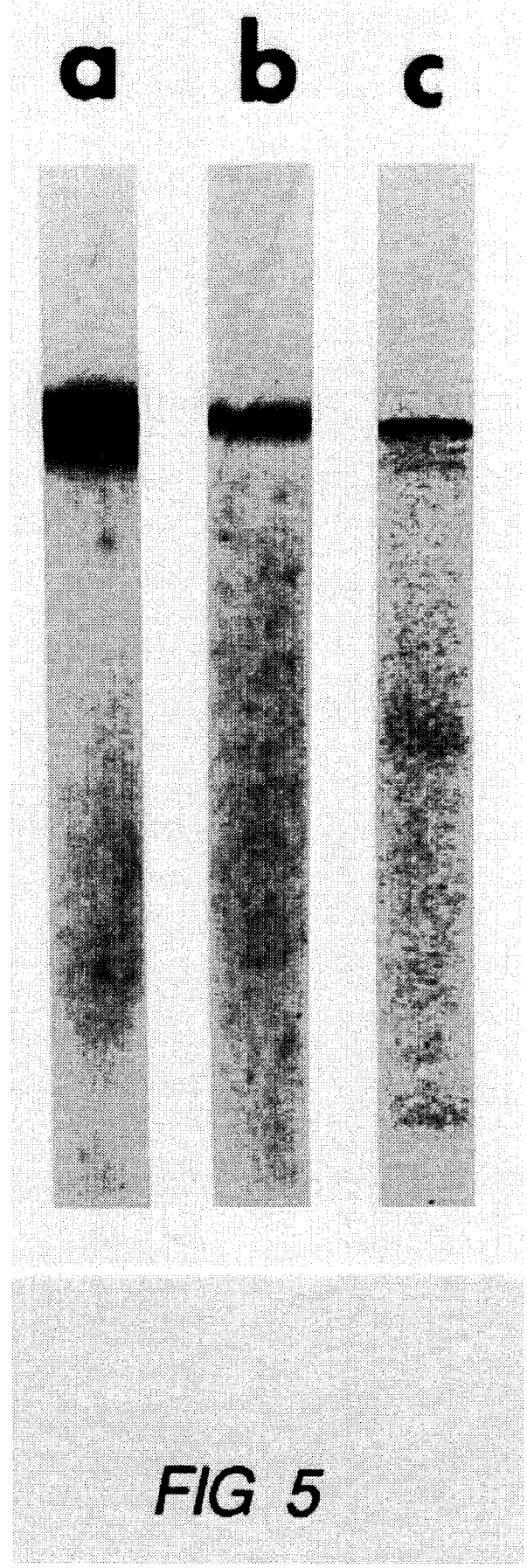
FIG. 5 illustrates the time course of inhibition of $^3$H-thymidine and $^3$H-uridine uptake by ConA-stimulated splenocytes.

The kinetics of DNA and RNA inhibition by SPN was examined to determine if the observed inhibition of DNA synthesis by SPN was also reflected in RNA synthesis and to determine the time course of inhibition by SPN as assessed by the incorporation of $^3$H-thymidine and $^3$H-uridine. Con A-stimulated (2 ug/ml) murine splenocytes (3×10$^5$ cells/well) were cultured in RPMI 1640 medium in the presence of 320 nM SPN or in its absence. At the beginning of the experiment 50 nCi of either $^3$H-thymidine or $^3$H-uridine was added to each well. At the indicated times the cells were harvested and the cell associated radioactivity was determined. The results indicated that SPN inhibited both DNA and RNA synthesis (FIG. 5). RNA synthesis was inhibited within 2–4 h of SPN addition whereas DNA inhibition occurred between 12–15 h after SPN addition. Since Con A-stimulated incorporation of $^3$H-thymidine routinely occurs between 12 to 18 h post-addition, these results were expected. It is significant that the inhibitory effects of SPN on splenocyte proliferation occurred very early (2–4 h) in the mitogen-stimulated activation of these cells.

EXAMPLE 7

Inhibition of Normal and Neoplastic Cell Proliferation

The effect of SPN on proliferation and cytotoxicity of a variety of cultured cells was examined. The cell lines (3–5×10$^6$ cells/ml) indicated in Table 7 were cultured at a density of 3–5×10$^6$ cells/ml for 48 h in the presence or absence of 3.7 ug/ml DEAE-SPN before adding 500 nCi/well $^3$H-thymidine and incubating a further 18 h. After harvest, cell-associated radioactivity was determined, and the precent inhibition calculated. Cell viability was determined by trypan blue exclusion.

The results in Table 7 show that SPN inhibited cell proliferation to varying degrees in neoplastic or transformed lymphoid, neuroendocrine and neural cells. Furthermore, the proliferation of fibroblast, epithelial cells, or monocytic cell lines was unaffected by SPN. Cytoxicity was not observed with any of the cell lines tested.

EXAMPLE 8

Inhibition of SPN Activity by Anti-SPN Antibodies and Affinity Purification of Suppressin Anti-SPN antibodies were used to affinity purify SPN from DEAE-SPN. One ml. of DEAE-SPN (113 ug/ml) was chromatographed on either an anti-SPN Sepharose 4B column (2 mg Ig/ml resin) or an underivitized Sepharose 4B control column, and the run-through tested in splenocyte proliferation assay. Affinity chromatography with anti-SPN Sepharose removed SPN-associated bioactivity in Con-A-stimulated proliferation assays while the sample of the control column retained the ability to inhibit splenocyte proliferation (78%). Moreover, SDS-PAGE analysis of the material that bound to the anti-SPN column showed a single band at 63 kDa when the gel was silver stained and confirmed that we had produced a monospecific polyvalent anti-SPN antibody which was useful to affinity purify SPN.

A further example of SPN purification by affinity chromatography is described below.

EXAMPLE 9

Suppressin Production by GH$_3$ Pituitary Cells

SPN was constitutively synthesized by a rat pituitary tumor cell line (GH$_3$). The conditioned media from GH$_3$ cells, cultured in the presence of $^{35}$S-methionine, was chromatographed on an anti-SPN antibody affinity column as indicated in the Section J of the General Methods section. SDS-PAGE analysis of the material in GH$_3$ conditioned media that bound to the anti-SPN affinity column showed a single stainable protein band (FIG. 6, Lane B) that had the same $M_r$ (63,000) as bovine affinity purified pituitary derived SPN (FIG. 6, Lane A). Autofluorographic analysis of this gel showed that the single polypeptide band was metabolically radiolabelled (FIG. 6, Lane C). Moreover, the affinity purified SPN from GH$_3$ conditioned media inhibited splenocyte proliferation 42% at a concentration 8.3×10$^{-9}$M. These experiments show that SPN is synthesized de novo and secreted by GH$_3$ cells. Moreover, SPN produced by these cells was functionally and immunologically similar to SPN isolated from bovine pituitary tissues.

TABLE 1

| | Enzymatic and Heat Treatment of BPE[a] | |
| --- | --- | --- |
| Sample Treatment | Mean Cell Associated $^3$H-dThd (±SEM) | % Inhibition |
| Control | 12,741 ± 968 | |
| BPE (untreated) | 2,552 ± 628 | 80 |
| Trypsin (25 units) | 12,844 ± 633 | 0 |
| Heat-Treatment | | |
| 45° C. | 2,358 ± 1,127 | 82 |
| 60° C. | 12,216 ± 763 | 0 |
| 80° C. | 12,002 ± 681 | 0 |
| 100° C. | 12,917 ± 872 | 0 |

[a]bovine pituitary extract

TABLE 2

Amino Acid Composition of SPN

| Amino Acid | Mole Percent |
|---|---|
| Ala | 7.5 |
| Arg | 4.9 |
| Asp or Asn | 9.7 |
| Cys | ND |
| Glu or Gln | 12.3 |
| Gly | 8.3 |
| His | 2.4 |
| Ile | 3.8 |
| Leu | 9.5 |
| Lys | 6.9 |
| Met | 0.3 |
| Phe | 3.9 |
| Pro | 6.2 |
| Ser | 7.3 |
| Thr | 7.0 |
| Trp | ND |
| Tyr | 3.3 |
| Val | 6.5 |

TABLE 3

ELISA Assay of Affinity Purified Anti-SPN Immunoglobulin

| Dilution | Pre-Immune Ig | Run-Through Ig Absorbance 405 nm | Bound Ig |
|---|---|---|---|
| 1:10 | 0.69 | 0.70 | >2.0 |
| 1:20 | 0.68 | 0.59 | >2.0 |
| 1:40 | 0.64 | 0.62 | >2.0 |
| 1:80 | 0.91 | 0.81 | >2.0 |
| 1:160 | 0.89 | 0.81 | 1.85 |
| 1:320 | 0.81 | 0.68 | 1.51 |
| 1:640 | 0.95 | 0.78 | 1.26 |
| 1:1280 | 0.91 | 0.92 | 1.04 |

TABLE 4

Effect of SPN on Mitogen-Stimulated Splenocytes

| SPN | Mitogen | $^3$H-dThd Incorporated[a] $\bar{x}$ ± SEM (cpm) | % Inhibition |
|---|---|---|---|
| + | PHA | 3,508 ± 417 | 92 |
| − | PHA | 43,220 ± 3,713 | |
| + | PWM | 4,376 ± 578 | 90 |
| − | PWM | 42,996 ± 2,050 | |
| + | Con A | 496 ± 33 | 99 |
| − | Con A | 35,396 ± 1,576 | |
| + | LPS | 35,554 ± 1,104 | 65 |
| − | LPS | 101,363 ± 1,315 | |

[a]The control and experimental sample size was 12

TABLE 5

Kinetics of SPN Inhibition of Con A-stimulated Splenocyte Proliferation

| Time of SPN Addition (h) | $^3$H-dThd Incorporated $\bar{x}$ ± SEM (cpm) | % Inhibition |
|---|---|---|
| 0 | 1,658 ± 151 | 98 |
| 6 | 21,062 ± 3,141 | 72 |
| 24 | 43,992 ± 3,060 | 43 |
| 48 | 64,196 ± 2,308 | 17 |
| Control | 77,303 ± 3,243 | — |

TABLE 6

Dose Response of Con A-Stimulated Splenocytes to SPN

| SPN Concentration | Cell Associated[a] H-dThd (cpm) | % Inhibition |
|---|---|---|
| none | 76,716 ± 869 | — |
| 3 × 10$^{-12}$ | 60,143 ± 4,182 | 22 |
| 1 × 10$^{-11}$ | 59,575 ± 3,805 | 22 |
| 3 × 10$^{-11}$ | 54,873 ± 2,108 | 28 |
| 1 × 10$^{-10}$ | 52,789 ± 2,390 | 31 |
| 3 × 10$^{-10}$ | 46,188 ± 3,796 | 40 |
| 1 × 10$^{-9}$ | 42,474 ± 818 | 45 |
| 3 × 10$^{-9}$ | 24,517 ± 2,267 | 68 |
| 1 × 10$^{-8}$ | 14,618 ± 904 | 81 |

[a]The sample size was 6

TABLE 7

Effect of SPN on Selected Cell Lines

| Cell Line | Origin | % Inhibition | Cytotoxic[a] |
|---|---|---|---|
| Molt 4 | Human T cell leukemia | 44 | — |
| HUT 78 | Human T cell lymphoma | no effect | — |
| CEM | Human T cell leukemia | 36 | — |
| H-9 | Human T cell lymphoma | 46 | — |
| BCL1 | Murine B cell leukemia | 38 | — |
| Y-1 | Murine adrenal tumor | 58 | — |
| NG108 | Murine neuroblastoma x glioma | 70 | — |
| GH3 | Rat pituitary tumor | 54 | — |
| WISH | Human amnion HeLa markers | 0 | — |
| L-cells | Murine fibroblast | 0 | — |
| CTLL-2 | Murine T-cell | 78 | — |
| HL60 | Promyelocytic leukemia | 0 | — |
| L1210 | Lymphocytic leukemia | 75 | — |
| EL-4 | Murine lymphoma | 71 | — |
| EL4/IL2 | Murine lymphoma | 69 | — |
| P388D$_1$ | Lymphoblast neoplasm | 0 | — |

[a]determined by trypan blue exclusion

TABLE 8

Sequential $(NH_4)_2SO_4$ Precipitation of SPN from Pituitary Extracts

| % Saturation | Amount of Protein (mg) | $^3$H-dThd (cpm) | % Inhibition |
|---|---|---|---|
| 25 | 1.5 | 12,344 ± 712 | 71 |
| 30 | 7.44 | 5,883 ± 338 | 86 |
| 40 | 3.12 | 43,384 ± 1,034 | 0 |
| 50 | 15.12 | 43,408 ± 934 | 0 |
| Supernatent | 154.65 | 41,907 ± 398 | 0 |
| Control | | 42,899 ± 496 | |

What is claimed is:

1. An antiproliferation factor comprising essentially purified and isolated mammalian suppressin (SPN) isolated from pituitary tissue wherein:

(a) said suppressin is tissue-specific for inhibiting cell proliferation of cells of lymphoid or neuroendocrine origin;

(b) said suppressin comprises a protein having at least one subunit of $M_r$ 63,000 determined under reducing conditions by SDS-polyacrylamide gel electrophoresis, an intrachain disulfide bond and a pI of about 8.1 and wherein said protein has an amino acid composition comprising:

| Amino Acid | Mole Percent |
|---|---|
| Ala | 7.5 |
| Arg | 4.9 |
| Asp or Asn | 9.7 |
| Cys | ND |
| Glu or Gln | 12.3 |
| Gly | 8.3 |
| His | 2.4 |
| Ile | 3.8 |
| Leu | 9.5 |
| Lys | 6.9 |
| Met | 0.3 |
| Phe | 3.9 |
| Pro | 6.2 |
| Ser | 7.3 |
| Thr | 7.0 |
| Trp | ND |
| Tyr | 3.3 |
| Val | 6.5 |

2. The factor of claim 1 wherein said factor comprises homogeneous suppressin from bovine pituitary tissue.

3. The factor of claim 1 wherein said factor comprises 35% ammonium sulfate-suppressin from bovine pituitary tissue.

4. The factor of claim 1 wherein said factor comprises DEAE-suppressin from bovine pituitary tissue.

5. An antibody to essentially purified and isolated mammalian suppressin isolated from pituitary tissue wherein:

(a) said suppressin is tissue-specific for inhibiting cell proliferation of cells of lymphoid or neuroendocrine origin;

(b) said suppressin comprises a protein having at least one subunit of $M_r$ 63,000 determined under reducing conditions by SDS-polyacrylamide gel electrophoresis, an intrachain disulfide bond and a pI of about 8.1 and wherein said protein has an amino acid composition comprising:

| Amino Acid | Mole Percent |
|---|---|
| Ala | 7.5 |
| Arg | 4.9 |
| Asp or Asn | 9.7 |
| Cys | ND |
| Glu or Gln | 12.3 |
| Gly | 8.3 |
| His | 2.4 |
| Ile | 3.8 |
| Leu | 9.5 |
| Lys | 6.9 |
| Met | 0.3 |
| Phe | 3.9 |
| Pro | 6.2 |
| Ser | 7.3 |
| Thr | 7.0 |
| Trp | ND |
| Tyr | 3.3 |
| Val | 6.5 |

6. An antibody to the antiproliferation factor of any one of the claims 1 or 2–4.

7. The antibody of claim 6 wherein said antibody is polyclonal or monoclonal.

8. The antibody of claim 5 wherein the mammalian suppressin is bovine suppressin.

9. The antibody of claims 5 or 8 wherein said antibody is a polyclonal or monoclonal antibody.

10. A pharmaceutical composition comprising a therapeutically effective amount of essentially purified and isolated homogeneous mammalian suppressin according to claim 1 admixed with a pharmacologically acceptable carrier.

11. A method of inducing regression or inhibition of tumor or cancer growth in mammals comprising administrating to said mammal in need of treatment essentially purified and isolated mammalian an antiproliferative factor of claim 1 in an amount effective to induce regression or inhibition of said tumor or cancer growth for a time and under conditions sufficient to induce said regression or inhibition.

12. The method of claim 11 wherein said tumor or cancer growth occurs in tissues of lymphoid, neuroendocrine or neural origin.

13. A method of treating arthritis comprising administrating to a mammal in need of treatment an antiproliferative factor of claim 1 in an amount effective to induce regression or inhibition of cells which cause arthritis for a time and under conditions sufficient to induce said regression or inhibition.

14. A method of treating an immune system disease comprising administering to a mammal in need of treatment an antiproliferative factor of claim 1 in an amount effective to induce regression or inhibition of cells which cause said immune system disease for a time and under conditions sufficient to induce said regression or inhibition.

15. A method of reducing or preventing transplantation or graft rejection comprising administering to a mammal in need of treatment an antiproliferative factor of claim 1 in an amount effective to induce regression or inhibition of cells which cause transplantation and graft rejection for a time and under conditions sufficient to induce said regression or inhibition.

16. The method of any one of claims 11, 12 and 13–15 wherein said effective amount of suppressin is administered to said mammal by intravenous, intramuscular, intranasal, intradermal, intraperitoneal, suppository or oral delivery.

17. The pharmaceutical composition of claim 10 in a unit dosage form in which the effective amount of mammalian suppressin is between about 10–1000 ug per dose.

18. The pharmaceutical composition of claim 10 wherein said mammalian suppressin is present in an amount sufficient to provide at least about 0.1 ug to about 2000 ug per kilogram body weight per day.

\* \* \* \* \*